(12) United States Patent
Church

(10) Patent No.: US 10,828,457 B2
(45) Date of Patent: Nov. 10, 2020

(54) HUMIDIFIER

(71) Applicant: Fisher & Paykel Healthcare Limited, Auckland (NZ)

(72) Inventor: Jonathan Mark Church, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 267 days.

(21) Appl. No.: 15/787,044

(22) Filed: Oct. 18, 2017

(65) Prior Publication Data

US 2018/0093066 A1 Apr. 5, 2018

Related U.S. Application Data

(62) Division of application No. 14/232,210, filed as application No. PCT/NZ2012/000122 on Jul. 11, 2012, now Pat. No. 9,802,023.

(60) Provisional application No. 61/507,896, filed on Jul. 14, 2011.

(51) Int. Cl.
| | |
|---|---|
| *A61M 16/16* | (2006.01) |
| *A61M 16/10* | (2006.01) |
| *A61M 16/14* | (2006.01) |
| *A61M 16/08* | (2006.01) |
| *A61M 16/00* | (2006.01) |

(52) U.S. Cl.
CPC .......... *A61M 16/16* (2013.01); *A61M 16/024* (2017.08); *A61M 16/0875* (2013.01); *A61M 16/109* (2014.02); *A61M 16/1075* (2013.01); *A61M 16/1095* (2014.02); *A61M 16/142* (2014.02); *A61M 16/107* (2014.02); *A61M 2205/364* (2013.01); *A61M 2205/3633* (2013.01); *F04C 2270/0421* (2013.01)

(58) Field of Classification Search
CPC ................ A61M 16/16; A61M 16/109; A61M 16/1095; A61M 16/142; A61M 16/0875; A61M 16/1075; A61M 16/107; A61M 2205/3633; A61M 2205/364; A61M 16/024; F04C 2270/0421
USPC ....................................................... 261/141
See application file for complete search history.

(56) References Cited

U.S. PATENT DOCUMENTS

| | | | |
|---|---|---|---|
| 3,655,346 | A | 4/1972 | Cotabish |
| 3,923,057 | A | 12/1975 | Chalon |
| 4,205,673 | A | 6/1980 | Wise |
| 4,232,667 | A | 11/1980 | Chalon |

(Continued)

FOREIGN PATENT DOCUMENTS

| | | |
|---|---|---|
| CN | 201036651 Y | 3/2008 |
| WO | WO 2011/151738 | 12/2011 |

OTHER PUBLICATIONS

European Communication for European Application No. 12811288.5, dated Jan. 4, 2018, 3 pages.

(Continued)

*Primary Examiner* — Charles S Bushey
(74) *Attorney, Agent, or Firm* — Knobbe, Martens, Olson & Bear, LLP

(57) ABSTRACT

A device is provided that humidifies breathing gas. The device has a chamber with an inlet and an outlet. A chemical heater is positioned within the chamber and a trigger activates the heater. The chamber can be a conduit with an inner wall and an outer wall with a reservoir defined therebetween. The chemical heater can be positioned within the reservoir.

22 Claims, 6 Drawing Sheets

(56) References Cited

U.S. PATENT DOCUMENTS

| | | | |
|---|---|---|---|
| 4,325,364 A | 4/1982 | Evans | |
| 4,597,917 A | 7/1986 | Lunsford | |
| 4,662,352 A | 5/1987 | Aviles, Jr. | |
| 4,829,997 A | 5/1989 | Douwens et al. | |
| 4,861,523 A | 8/1989 | Beran | |
| 4,910,384 A | 3/1990 | Silver | |
| 4,917,119 A | 4/1990 | Potter | |
| 5,205,278 A | 4/1993 | Wang | |
| 5,360,002 A | 11/1994 | Smith | |
| 5,495,847 A | 3/1996 | Hu | |
| 5,992,413 A | 11/1999 | Martin | |
| 6,363,930 B1 | 4/2002 | Clawson | |
| 6,463,925 B2 | 10/2002 | Nuckols | |
| 6,557,551 B2 * | 5/2003 | Nitta | A61M 16/16 128/201.13 |
| 6,877,510 B2 | 4/2005 | Nitta | |
| 7,047,970 B2 | 5/2006 | Umeda | |
| 7,198,255 B2 * | 4/2007 | Chiba | A61M 11/06 128/200.13 |
| 8,567,395 B2 | 10/2013 | Savona | |
| 8,944,056 B2 * | 2/2015 | Virr | A61M 16/0875 128/204.17 |
| 9,802,023 B2 * | 10/2017 | Church | A61M 16/16 |
| 2009/0250055 A1 | 10/2009 | Radomski et al. | |
| 2010/0083965 A1 | 4/2010 | Virr et al. | |
| 2011/0000485 A1 | 1/2011 | Gray et al. | |
| 2011/0082416 A1 | 4/2011 | Iranitalab et al. | |

OTHER PUBLICATIONS

Written Opinion and International Search Report ; PCT/NZ2012/000122; dated Sep. 24, 2012; 10 pages.

Extended European Search Report for European Application No. 12811288.5, dated Feb. 16, 2015, 6 pages.

First Chinese Office Action for Chinese Patent Application No. 201280044487.2; dated Aug. 6, 2015 in 14 pages (with English translation).

Chinese Office Action for Chinese Patent Application No. 201610009908.8 in 13 pages (English Translation).

European Search Report for European Application No. 19179259 dated Oct. 16, 2019 in 3 pages.

* cited by examiner

HUMIDIFIER

FIELD OF THE INVENTION

The present invention relates to a device for humidifying breathing gases for delivery to a user, and more particularly to a respiratory humidifier for heating and humidifying breathing gases prior to delivery to a user.

BACKGROUND OF THE INVENTION

A breathing system is set of medical components that prepare and deliver breathing gases to a user or patient. The components comprising the breathing system may vary depending on the application, type of treatment being provided and/or the location the treatment is taking place.

A typical breathing system may comprise a source of breathing gases (such as a hospital supply, mechanical ventilator, home blower unit or resuscitation bag), a user interface for administering the breathing gases to the user (such as a mask or nasal cannula) and a breathing tube coupling the gas source to the user interface. Some breathing systems may also incorporate a heater and/or a humidifier for treating the breathing gases prior to delivery. Ideally, the breathing gases are heated to about 37° C. to match the user's core temperature.

The gases may be humidified to reduce discomfort and other more serious side effects caused by the removal of moisture from the patient respiratory system. Humidification is more important in situations where breathing gases are heated, as the elevated temperature increases the gases capacity to remove moisture. The heating and humidification processes may be partially or completely combined in a breathing system.

Many existing humidifiers or humidification systems for breathing gases are reliant on electrically powered systems for operating heaters of the gases and associated humidifying techniques. However, in field operations or situations where electrical power is not available, or even for ease of portability, it may be useful to provide a device for humidifying breathing gases that is capable of operating independently of a source of electrical power.

It is, therefore, an object of the present invention to provide, or to at least go some way towards providing a device for humidifying breathing gases for delivery to a user, or to at least provide the public and/or medical profession with a useful choice.

SUMMARY OF INVENTION

In one aspect, the invention broadly consists in a device for humidifying breathing gas comprising: a conduit arrangement, the conduit arrangement comprising an inner wall and an outer wall, the inner wall defining a gas transport pathway, the gas transport pathway including an inlet and an outlet, the outer wall surrounding at least a section of the inner wall, wherein a reservoir is defined between the inner and outer walls, and a chemical heater is located within the reservoir, and wherein a source of humidifying fluid is contained by the outer wall, and a trigger is configured for activating the chemical heater to generate heat.

Preferably the inlet is connectable with, or fluidly connectable to, a gas supply, and the outlet is connectable with, or fluidly connectable to, a user interface or a user gas delivery device.

Preferably the chemical heater is disposed for thermal exchange with at least a part of one or more of, the inner wall or at least the section of inner wall, gas passing through the gas transport pathway, or humidifying fluid.

Preferably the source of humidifying fluid is provided, at least, from within, or by, one or more of, the inner wall or at least the section of inner wall, and/or the reservoir, for humidifying gas passing through the gas transport pathway.

Preferably in use, on activation the chemical heater generates heat for heating of gas passing through the gas transport pathway and/or promotes humidification fluid uptake by the gas.

Preferably the inner wall is breathable.

Preferably the inner wall allows passage of humidification fluid to gas passing through the gas transport pathway.

Preferably the inner wall allows passing of humidification fluid vapour to gas passing through the gas transport pathway.

Preferably the inner wall stores or is capable of storing humidification fluid, such that, in-use, gas passing through the gas transport pathway takes up at least a portion of the stored humidification fluid.

Preferably the inner wall is pre-charged with humidification fluid prior to use.

Preferably the reservoir is capable of storing humidification fluid, such that, in-use, the humidification fluid (or vapour thereof) and gas passing through the gas transport pathway are fluidly contactable.

Preferably the outer wall is impermeable to humidification fluid (or vapour thereof).

Preferably the outer wall comprises insulation or is heat insulated.

Preferably the chemical heater is a chemical agent that, when activated, is exothermic.

Preferably the chemical heater is a supersaturated salt solution capable of an exothermic crystallization when activated.

Preferably the chemical heater comprises, or is, sodium acetate.

Preferably the trigger is a mechanical actuator that, when actuated, provides for a nucleation site within the chemical heating element to initiate a crystallisation.

Preferably the trigger is a metallic disk.

Preferably the metallic disk is located within the heating element.

Preferably the device is non-electrically powered.

Preferably the device is a portable humidifier.

Preferably the gas supply is a source of breathing gas.

Preferably the outer wall is co-axial with and surrounding of the inner wall.

Preferably an inner tube forms the inner wall, and an outer tube forms the outer wall.

Preferably the device comprises a part of a medical breathing circuit, or a medical resuscitation system.

Preferably the device is single use.

In another aspect, the invention broadly consists in a device for humidifying breathing gas comprising: an inner tube defining a gas transport pathway, the pathway including an inlet connectable with, or fluidly connectable to, a gas supply, and an outlet connectable with, or fluidly connectable to, a user interface or a user gas delivery device, an outer tube surrounding the inner tube or at least a section of the inner tube, and a reservoir is defined between walls of the inner tube and the outer tube, and a chemical heater is located within the reservoir, the chemical heater disposed for thermal exchange with one or more of an inner wall of the inner tube or at least the section of the inner wall of the inner tube, gas passing through the gas transport pathway, a humidifying fluid, and wherein a source of humidifying fluid is provided, at least, from within, or by, one or more of, the inner wall of the inner tube or at least the section of the inner wall of the inner tube, and/or the reservoir, for humidifying gas passing through the gas transport pathway, a trigger configured for activating the heating element to generate heat, such that, in use, on activation the chemical heater generates heat for heating of gas passing through the gas transport pathway and/or promotes humidification fluid uptake by the gas.

In another aspect, the invention broadly consists in a device for humidifying breathing gas comprising: a chamber for humidifying gas, the chamber having an inlet and an outlet, a chemical heater disposed for thermal exchange with at least a part of the chamber, and a trigger configured for activating the chemical heater to generate heat, and a source of humidification fluid dispensable to the chamber.

Preferably the inlet is connectable with, or fluidly connectable to, a gas supply, and the outlet is connectable with, or fluidly connectable to, a user interface or a user gas delivery device.

Preferably in use, on activation the chemical heater generates heat for heating of gas passing through the chamber from the inlet to the outlet and/or promotes humidification fluid uptake by the gas.

Preferably the trigger comprises at least a portion for mechanically initiating activation of the heating element to generate heat.

Preferably the trigger comprises a reservoir for storing humidification fluid to be supplied to the chamber.

Preferably the trigger is configured for activating the chemical heater and for dispensing the source of humidification fluid to the chamber.

Preferably activation of the trigger activates the chemical heater and simultaneously dispenses the source of humidification fluid to the chamber.

Preferably the trigger comprising a humidification fluid reservoir, the fluid reservoir sealed from the chamber by a seal prior to use, and where the fluid reservoir is unsealed from the chamber for use.

Preferably the fluid reservoir seal is broken or pierced when the trigger is operated.

Preferably the trigger comprises a plunger having a humidification fluid reservoir sealed from the chamber when in a pre-use configuration, and where fluid stored in the fluid reservoir is unsealed and dispensed into the chamber when in an in-use configuration.

Preferably the trigger comprises at least a portion activating the heater element to generate heat when moved from a pre-use configuration to an in-use configuration.

Preferably the chemical heater is disposed in thermal exchange with a base or base portion of the chamber.

Preferably the base or base portion is a heat conductive base forming a floor to the chamber.

Preferably a conductive heating surface is disposed between the chemical heater and a floor to the chamber.

Preferably the chemical heater is a chemical agent that, when activated, is exothermic.

Preferably the chemical heater is a supersaturated salt solution capable of exothermic crystallization when activated.

Preferably the chemical heater element comprises, or is, sodium acetate.

Preferably the trigger is a mechanical actuator that, when actuated, provides for a nucleation site within the chemical heating element to initiate a crystallisation.

Preferably the trigger is a metallic disk.

Preferably the metallic disk is located within the heating element.

Preferably the device is non-electrically powered.

Preferably the device is a portable humidifier.

Preferably the gas supply is a source of breathing gas.

Preferably the device comprises a part of a medical breathing circuit, or a medical resuscitation system.

Preferably the device is single use.

Preferably the inlet and outlet define a gas transport pathway therebetween.

In another aspect, the invention broadly consists in a device for humidifying breathing gas comprising: a chamber for humidifying gas, the chamber having an inlet connectable with, or fluidly connectable to, a gas supply, and an outlet connectable with, or fluidly connectable to, a user interface or a user gas delivery device, a chemical heater disposed for thermal exchange with at least a part of the chamber, and a trigger configured for activating the chemical heater to generate heat, and a source of humidification fluid dispensable to the chamber, such that, in use, on activation the humidification fluid is dispensed to the chamber and the chemical heater generates heat for heating of gas passing through the chamber and/or promotes humidification fluid uptake by the gas.

In another aspect, the invention broadly consists in a method for humidifying breathing gas comprising: providing a gas transport pathway between an inlet and an outlet, and providing a chemical heater disposed in thermal exchange with at least a part of the gas transport pathway, and a trigger for activating the chemical heater to generate heat, and providing a source of humidification fluid, the humidification fluid being made available for uptake by gas passing through the gas transport pathway upon activation of the chemical heater.

Preferably an inner wall of a conduit arrangement defines the gas transport pathway, the conduit arrangement comprising of the inner wall and an outer wall, the outer wall surrounding at least a section of the inner wall, wherein a reservoir is defined between the inner and outer walls, the chemical heater located within the reservoir, and wherein the source of humidifying fluid is contained by the outer wall, and the trigger is configured for activating the chemical heater to generate heat.

Preferably in use, on activation by the trigger, the chemical heater generates heat for heating of gas passing through the gas transport pathway and/or promotes humidification fluid uptake by the gas.

Preferably wherein the gas transport pathway is defined between the inlet and the outlet of a chamber, with a chemical heater disposed for thermal exchange with at least a part of the chamber, and wherein the source of humidification fluid is dispensable to the chamber, and the trigger is configured for activating the chemical heater to generate heat.

Preferably in use, on activation by the trigger, the humidification fluid is dispensed to the chamber and the chemical heater generates heat for heating of gas passing through the chamber and/or promotes humidification fluid uptake by the gas.

Preferably the inlet is connectable with, or fluidly connectable to, a gas supply, and the outlet is connectable with, or fluidly connectable to, a user interface or a user gas delivery device, such that in an in-use configuration, gas passing through the gas transport pathway is heated and/or is humidified by uptake of humidification fluid.

Preferably the gas supply is from a blower or a ventilator or a resuscitator.

Preferably the user interface is a mask or a nasal cannula.

Preferably the user gas delivery device comprises a part of a medical breathing circuit, such as a further section of conduit or other gas delivery device for supply humidified gas to a user.

The term "comprising" as used in this specification means "consisting at least in part of". When interpreting each statement in this specification (and claims-again delete if not needed) that includes the term "comprising", features other than that or those prefaced by the term may also be present. Related terms such as "comprise" and "comprises" are to be interpreted in the same manner.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The invention consists in the foregoing and also envisages constructions of which the following gives examples only.

BRIEF DESCRIPTION OF THE DRAWINGS

Preferred embodiments of the invention will be described by way of example only and with reference to the drawings, in which.

DETAILED DESCRIPTION OF THE PREFERRED EMBODIMENT

Figure 1:
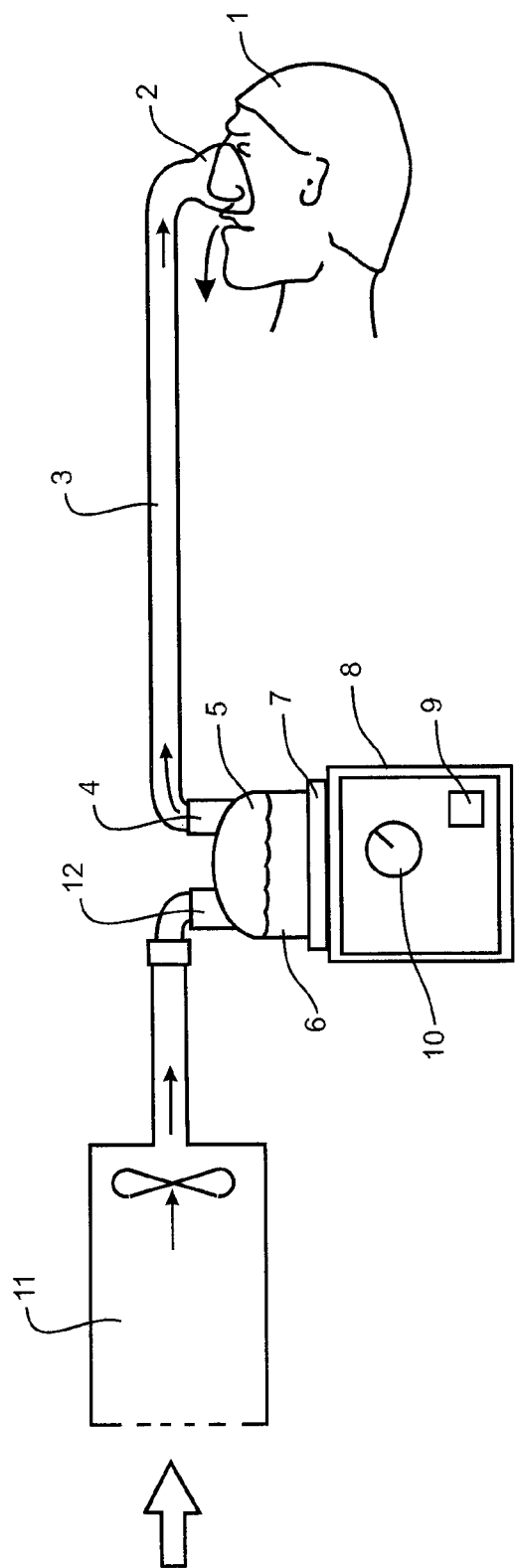
FIG. 1 is a schematic of a prior art system for providing humidifying breathing gases to a patient or user.
Figure 2:
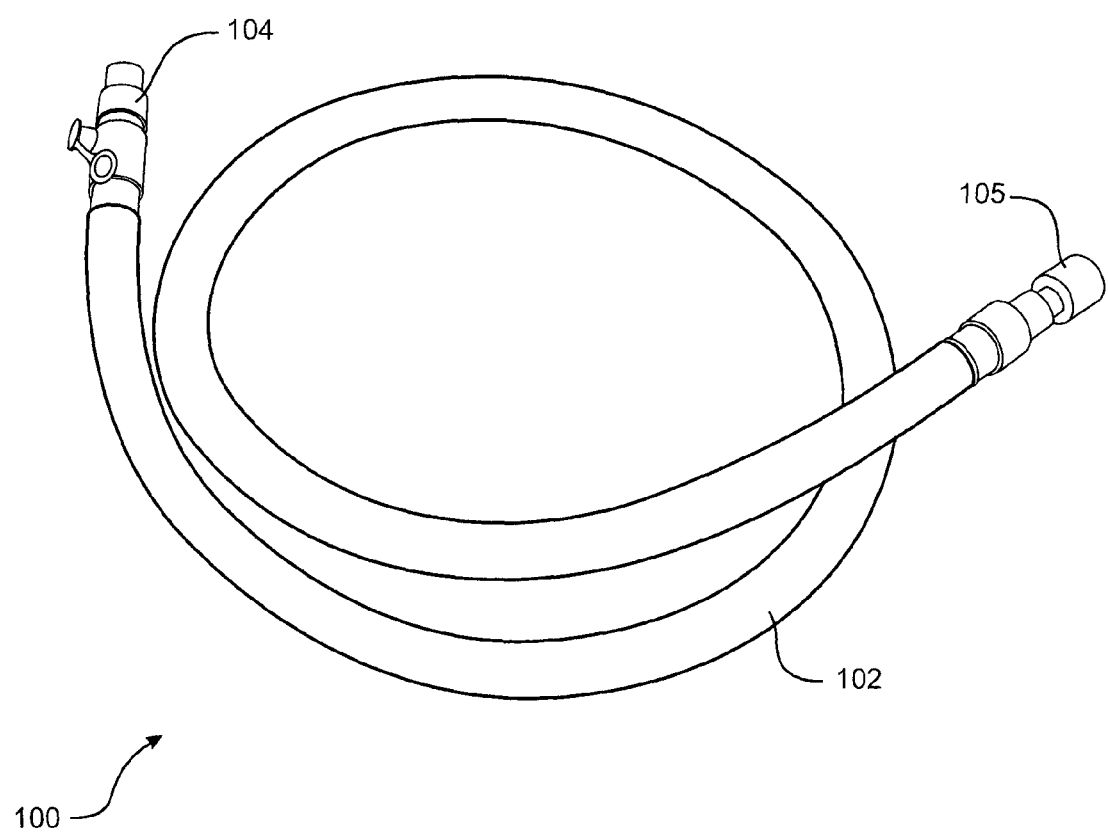
FIG. 2 shows a device comprising a conduit arrangement for humidifying breathing gases.
Figure 3:
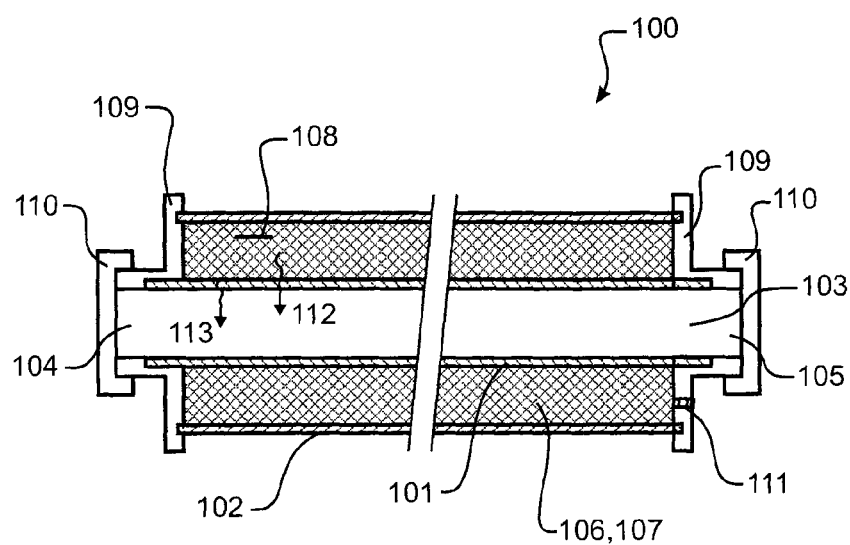
FIG. 3 is a cross sectional representation of a device comprising a conduit arrangement for humidifying breathing gases.

FIG. 1 schematically represents a typical respiratory humidifier system for providing humidifying breathing gases to a patient or user 1. Humidified gases are provided to the user through a patient interface 2 connected to a humidified gases transportation pathway or inspiratory conduit 3. Inspiratory conduit 3 is connected to the outlet 4 of a humidification chamber 5 which contains a volume of water 6. Humidification chamber 5 is preferably formed from a plastics material and may have a highly heat conductive base (for example an aluminium base) which is in direct contact with a heater plate 7 of humidifier 8. Humidifier 8 is provided with control means or electronic controller 9 which may comprise a microprocessor based controller executing computer software commands stored in associated memory.

Controller 9 receives input from sources such as a user input interface or dial 10 through which a user of the device may, for example, set a predetermined required value of humidity or temperature of the gases supplied to patient 1. The controller may also receive input from other sources, for example temperature and/or flow velocity sensors. In response to the user set humidity or temperature value input via dial 10 and the other inputs, controller 9 determines when (or to what level) to energise heater plate 7 to heat the water 6 within humidification chamber 5. As the volume of water 6 within humidification chamber 5 is heated, water vapour begins to fill the volume of the chamber above the water's surface and is passed out of the humidification chamber 5 outlet 4 with the flow of gases (for example air) provided from a gases supply, for example a blower 11, which enters the chamber through inlet 12. Exhaled gases from the patient's mouth are passed directly to ambient surroundings in FIG. 1.

A prior art humidifier may not be easily transportable. Furthermore, prior art humidifiers require an external electrical power source to power the humidifier controller and for energising the heater plate. It would be useful to be able to provide a device for humidifying breathing gases, and yet that is portable and not reliant upon an electrical source for operation.

Such a device would advantageously be capable of providing sufficiently fast start-up time to be useful, for example in emergency situations, such as in hospitals, accident and emergency wards or in out of hospital operations, such as field operations or in remote locations.

It would also be useful to be able to provide a self-contained device for humidifying breathing gas that does not require additional parts or components for provision of a heater to heat gas or a separate supply of fluid used as the humidification fluid for breathing gases that can be passed through the device.

Accordingly, the devices of this invention aim to go at least some way towards addressing the above details.

Conduit Arrangement

With reference to FIGS. 2 to 5, in a first embodiment there is provided a device 100 for humidifying breathing gas. The device comprises a conduit arrangement. The conduit arrangement comprises an inner wall 101 and an outer wall 102. The inner wall defines a gas transport pathway 103. The gas transport pathway includes an inlet 104 and an outlet 105. A flow restrictor may be provided in the inlet 104 or outlet 105 so that for any given input pressure the flow rate of gas passing through the device is controlled or limited to an appropriate level. Preferably each end of the device is terminated with a connector 109 providing or forming the inlet 104 and outlet 105. For example connectors 109 may be over-moulded to the ends of the inner and outer walls. Preferably each end of the device, that is the inlet and outlet, are provided with protective caps 110 to prevent contamination of the gas transport pathway. Caps 110 are preferably not removed until the time the device is put to use.

The outer wall surrounds at least a section of the inner wall. A reservoir 106 is defined between the inner and outer walls. A chemical heater 107 is located within the reservoir 106. A source of humidifying fluid for the device 100 is contained within the device by the outer wall 102. And, a trigger 108 is configured for activating the chemical heater to generate heat.

The inlet 104 is connectable with, or fluidly connectable to, a gas supply (such as bellows, a ventilator or a blower), while the outlet 105 is connectable with, or fluidly connectable to, a user interface or a user gas delivery device (such as for example a face mask, nasal cannula or other patient delivery device like that described with reference to FIG. 1).

The chemical heater 107 is provided such that it is disposed for thermal exchange with at least a part of one or more of: the inner wall 101 or at least the section of inner wall, gas passing through the gas transport pathway, a humidifying fluid 106. For example, the chemical heater is contained or retained within the reservoir defined between the inner wall and the outer wall, in this manner contacting substantially sufficient region of the inner wall to allow heat transfer or exchange with gas passing through the transport pathway as indicated by arrow 112. Similarly, the chemical heater can act to promote vaporisation of humidification fluid, and may drive that vapour into the transport pathway for uptake by the gas passing therethrough, as indicated by arrow 113.

The source of humidifying fluid can be provided, at least, from within, or by, one or more of, the inner wall or at least the section of inner wall, and/or the reservoir, for humidifying gas passing through the gas transport pathway. For example, the device can be pre-charged with humidification fluid, prior to use of the device. In this manner, the device can be prepared (constructed) and pre-charged with a sterile humidification fluid, then stored ready for use. For example, where the inner wall or at least a section of the inner wall is breathable or porous to humidification fluid, the inner wall may, in a pre-charged (i.e. pre-use of the device) configuration, be charged with or store humidification fluid. For example the inner wall may be pre-charged with humidification fluid by adding a predetermined volume of humidification fluid to the gas transport pathway prior to fixing caps 110 to connectors 109 during manufacture of the device. The humidification fluid will soak into the material forming the inner wall for subsequent heating and evaporation through heating provided by the chemical heater during use.

During an in-use mode, heat generated by the chemical heater can promote humidification fluid to vaporise and pass into the gas transport pathway for uptake by the gas. In some variations, it may be that humidification fluid may be, or additionally, retained within the reservoir for subsequent supply to the breathable or porous inner wall and for supply as vapour or uptake by the gas passing through the transport pathway. For example, the reservoir may be pre-charged with fluid via a pre-charge port 111 formed in the connector 109 forming the inlet or outlet. The port 111 is subsequently sealed or plugged to store the fluid within the reservoir.

In use, on activation of the chemical heater 107, heat is generated. That heat is used for heating of gas passing through the gas transport pathway and/or promoting the uptake of humidification fluid by the gas. In this manner, a gas supplied or delivered to the inlet is heated and humidified, for example heated to a temperature such that gas delivered to a patient may be about 37° C. and of a relative humidity suitable for medical or breathing application. It will be appreciated the gas may be heated to a temperature above 37° C. such that a temperature drop from the device to the point of delivery to a user or patient provides gas at about 37° C. It will also be appreciated that providing a warmed, humidified gas to a user for breathing is more preferable than a cold, dry gas. The benefits of providing warmed and humidified gas to users are generally known for medical application.

Further however, the ability to provide a device capable of delivering such results, without the need for an external electrical power source, is particularly advantageous.

The ability to provide a portable device, capable of use in the field, or in situations where a rapid response for heating and humidification of breathing gases is needed is also particularly advantageous.

The inner tube is advantageously of a breathable material or construction. In this manner, the inner wall or a wall of an inner tube defining the gas transport pathway allows for the passage of humidification fluid (or its vapour) to the gas pathway. As mentioned above, the inner wall or a wall of the inner tube is capable of storing at least a portion of humidification fluid that may be subsequently brought into fluid contact with gas passing through the gas pathway. For example, in one form, the inner wall or inner wall of the inner tube can be pre-charged with humidification fluid prior to use or activation of the device.

In addition to the humidification fluid retained or stored by the wall, or even in an alternative form, for example, the reservoir may be capable of storing at least a portion of humidification fluid, such that, in-use, the humidification fluid (or vapour thereof) and gas passing through the gas transport pathway are fluidly contactable. In these examples, when the chemical heating element is activated, and heat is generated, at least a portion of the stored humidification fluid may be turned into vapour, that vapour can migrate or permeate through to the gas transport pathway, or at least to an inside surface of the inner wall for subsequent humidification of gas passing through the gas transport pathway.

In respect of the above forms, it will be appreciated that materials enabling or which facilitate the permeation or migration of humidification fluid, or vapour, to fluidly contact with gas passing through the transport pathway may be suitable. The chemical heating element provides a heated driver for vapour generation and for warming of the gas passing through the transport pathway.

In providing for a breathable inner tube, the outer wall or an outer wall of an outer tube, or at least an external wall of an outer tube, should be formed or constructed to be impermeable to humidification fluid (or its vapour). In this manner, humidification fluid is preferably not lost to the surrounding environment from the device. Should humidification fluid be lost, then the overall quantity of humidification fluid capable of being used for humidification of gases is impacted and reduced. That may otherwise limit the useful storage or shelf-life of such a device.

In various embodiments, the inner wall can allow passing or passage of humidification fluid vapour from the inner wall to gas passing through the gas transport pathway 103. Where the inner wall stores or is capable of storing humidification fluid, during use, gas passing through the gas transport pathway can take up at least a portion of the stored humidification fluid. The inner wall can be pre-charged with humidification fluid prior to use.

The outer wall (or external wall of an outer tube) and inner wall (or inner wall of an inner tube) are preferably formed or constructed so as to retain or contain the chemical heating element or the agent or components forming the heating element.

The outer wall may be insulated or comprise insulation. An insulated outer wall can be useful for a variety of reasons, including minimising heat loss from the chemical heater element when it is activated, or minimising the possibility that the outer wall becomes hot to the touch (for safety or handling purposes).

The chemical heater may comprise or is a chemical agent that, when activated, is exothermic or generates heat.

In one example, the chemical heater may be a supersaturated salt solution capable of undergoing an exothermic reaction, such as during a crystallization process, that process being carried out or initiated when activated by a trigger. The chemical heater element may for example be sodium acetate (e.g. a supersaturated solution of sodium acetate that when activated, undergoes an exothermic crystallisation process).

The trigger can be any suitable mechanism that activates the chemical heater to begin generating heat. In various forms however, the trigger can be a mechanical actuator that, when actuated, provides for a nucleation site within the chemical heating element to initiate a crystallisation.

For example, the trigger may be a metallic disk with striations that is optionally located within the chemical heater or a part thereof. Where sodium acetate is used, the metallic disk when triggered by being bent or deformed, may release a particle that initiates an exothermic crystallisation process.

The disk or position of the disk may be identifiable from the outside of the device. The disk may be activated by a user by, for example, squeezing the outer tube wall to elastically deform the outer tube wall to deform the disk.

In an alternative form the trigger may comprise a plastic part located within the chemical heater that can be flexed and snapped to produce a shard to activate the chemical heater.

In a further alternative form a plunger can be pushed or pierced through the wall of the outer tube. The plunger can be coated with crystals that initiate the exothermic chemical heater.

It may also be desirable to position the trigger in a position that best avoids accidental activation prior to actual use. The trigger may also comprise of an indicator to visually display whether the trigger can be activated or not.

ALTERNATIVE EMBODIMENT

Figure 4:
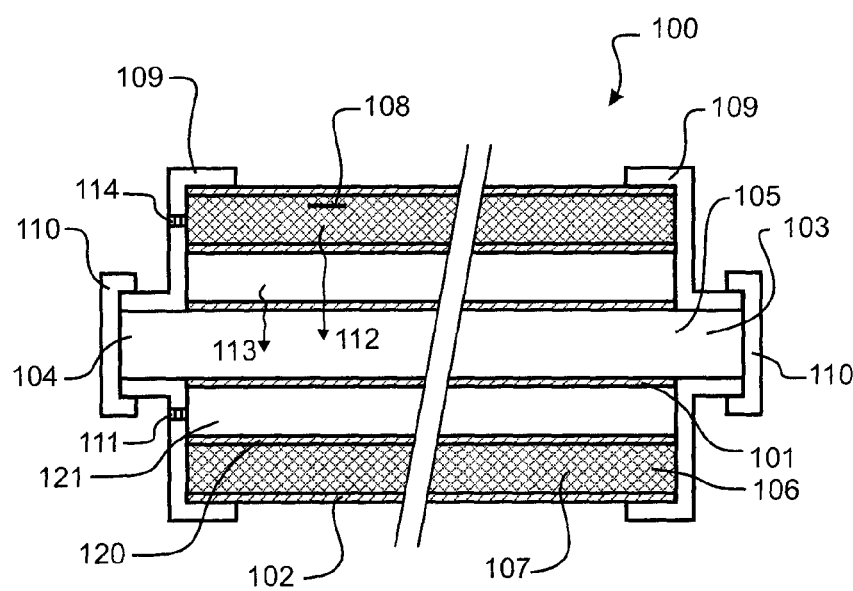
FIG. 4 is a cross sectional representation of another form of a device comprising a conduit arrangement for humidifying breathing gases.

With reference to FIG. 4, in an alternative form the reservoir 106 for storing the chemical heater is defined between the outer wall 102 and an intermediate wall 120 located intermediate between the inner wall 101 and the outer wall 102. In this embodiment a second reservoir 121 is formed between the intermediate wall 120 and the inner wall 101. The humidification fluid may be stored or contained for use in the second reservoir 121, or the second reservoir and the inner wall 101. For example, the second reservoir 121 may be pre-charged with fluid via a pre-charge port 111 formed in the connector 109 forming the inlet or outlet. The port 111 is subsequently sealed or plugged to store the fluid within the reservoir. In this alternative embodiment, the chemical heater is fluidly separated from the humidification fluid by the intermediate wall 120. For example, the first reservoir 106 may be pre-charged with a chemical heater via a pre-charge port 114 formed in the connector 109 forming the inlet or outlet. The port 114 is subsequently sealed or plugged to store the chemical heater within the reservoir.

Preferably the intermediate wall is highly thermally conductive so that heat generated by the chemical heater once activated by the trigger 108 transfers across the intermediate wall to heat the fluid within the second reservoir 121 and/or the inner wall. For example the intermediate wall could be formed from a metal foil.

Figure 5:
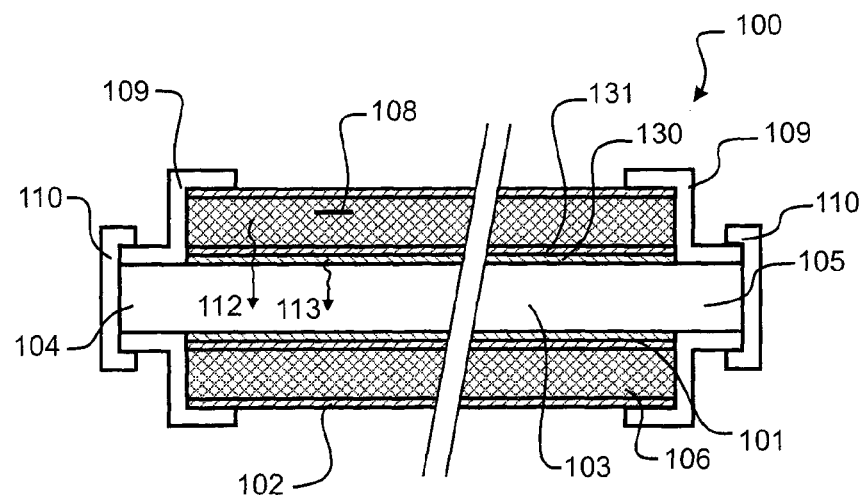
FIG. 5 is a cross sectional representation of yet another form of a device comprising a conduit arrangement for humidifying breathing gases.
Figure 6:
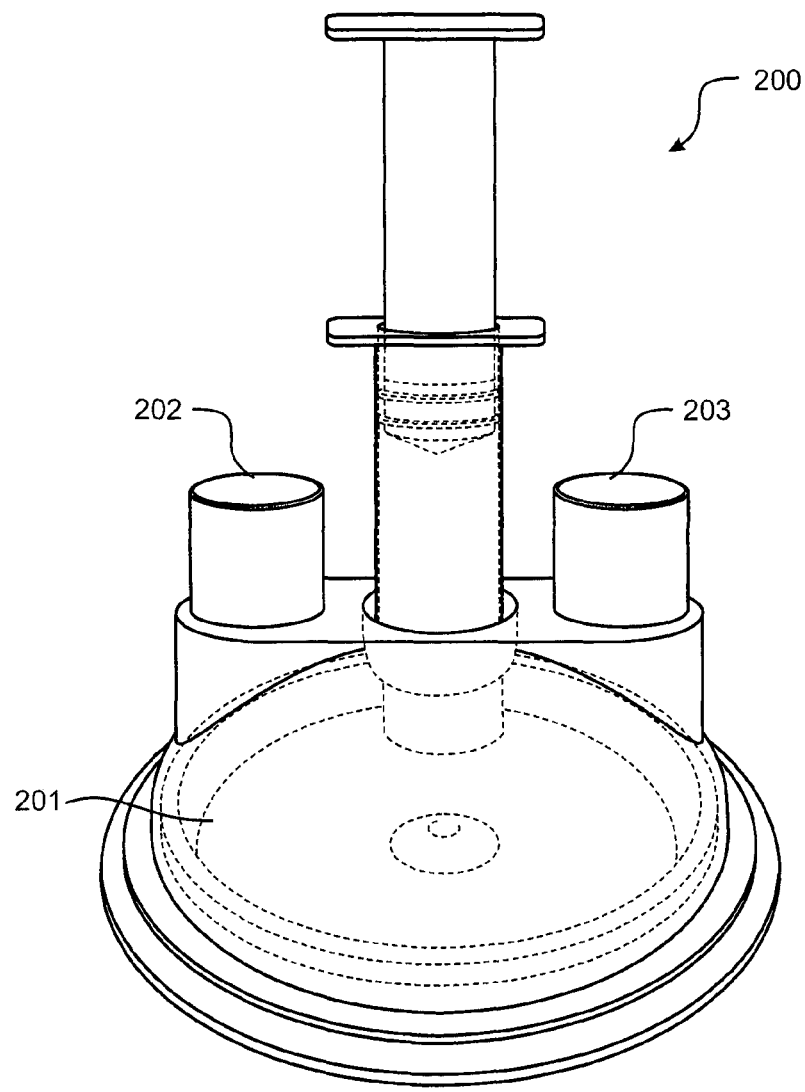
FIG. 6 shows a device comprising a chamber for humidifying breathing gas.
Figure 7:
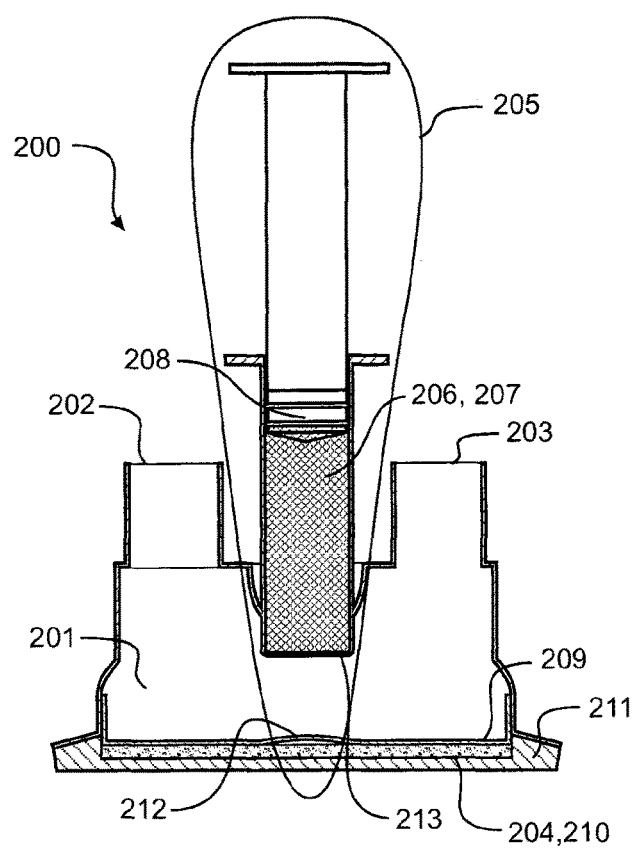
FIG. 7 is a cross sectional representation of the device of FIG. 6 in a pre-charged or pre-use state.

In a further alternative form illustrated in FIG. 5, the inner wall 101 may comprise a multi layered construction. An inner layer 130 comprises a porous material capable of retaining or storing humidification fluid. And an outer layer 131 comprises a highly conductive material capable of transferring heat but preventing transfer of fluid or vapour. The outer layer of the inner wall fluidly separates the humidification fluid from chemical heater. The outer layer of the inner tube could be metal foil or a coating on an outer surface of the inner wall 101.

As described above, the device comprises an inner wall 101 and an outer wall 102, and in this respect, the walls may be the walls of an inner tube and an outer surrounding co-axial tube.

For example, an inner tube can form the inner wall, and an outer tube forms the outer wall. In this respect, there may be provided a device for humidifying breathing gas comprising an inner tube defining a gas transport pathway. The pathway can include an inlet 104 connectable with, or fluidly connectable to, a gas supply, and an outlet 105 connectable with, or fluidly connectable to, a user interface or a user gas delivery device.

An outer tube may be coaxial with and surrounding of the inner tube or at least a section of the inner tube. A reservoir being defined between walls of the inner tube and the outer tube, and a chemical heater is located within the reservoir. Alternatively the device may comprise an intermediate wall or tube 120 positioned intermediate between the inner wall 101 and the outer wall 102, the reservoir being formed between the intermediate wall and the outer wall.

The chemical heater is disposed for thermal exchange with one or more of an inner wall of the inner tube or at least the section of an inner wall of the inner tube, gas passing through the gas transport pathway, a humidifying fluid, a wall of the intermediate tube or at least the section of a wall of the intermediate tube.

A source of humidifying fluid is provided, at least, from within, or by, one or more of, the inner wall of the inner tube or at least the section the inner wall of the inner tube, and/or the reservoir, and/or the second reservoir formed between the intermediate wall and the inner wall, for humidifying gas passing through the gas transport pathway. And, a trigger is configured for activating the heating element to generate heat, such that, in use, on activation the chemical heater generates heat for heating of gas passing through the gas transport pathway and/or promotes humidification fluid uptake by the gas.

In one further form, the embodiment described above may be a co-axial tubing with chemical heater located in a reservoir located therebetween, and where humidifying fluid is retained by a wall of the inner tube and/or within the reservoir, such that activation of the chemical heater operates as a driver for driving humidifying fluid vapour into a gas transport pathway for entrainment or uptake by the gas passing therethrough.

Chamber Configuration

With reference to FIGS. 6 to 10, in a second embodiment, there is provided a device for humidifying breathing gas.

The device 200 comprises a chamber 201 for humidifying gas, the chamber having an inlet 202 and an outlet 203. A filter or valve may be included in the outlet 203 to prevent or limit fluid held in the chamber 201 reaching the patient, for example in the event the chamber was tipped from a typical in use orientation to cause fluid in the chamber to spill into the chamber outlet. A chemical heater 204 is disposed for thermal exchange with at least a part of the chamber, and a trigger 205 configured for activating the chemical heater to generate heat. A source of humidification fluid 206 is provided that is dispensable to or into the chamber 201.

The inlet is connectable with, or fluidly connectable to, a gas supply (such as bellows, a ventilator or a blower), and the outlet is connectable with, or fluidly connectable to, a user interface or a user gas delivery device (such as for example a face mask, nasal cannula or other patient delivery device described with reference to FIG. 1).

In use, on activation the chemical heater generates heat for heating of gas passing through the chamber from the inlet to the outlet and/or for promoting the uptake of humidification fluid by the gas.

The trigger can comprise of at least a portion or a part that is capable of mechanically initiating activation of the chemical heater to generate heat.

The trigger may also or separately comprise of a reservoir for storing the humidification fluid 206 to be supplied or dispensed to or into the chamber 201. For example, the trigger 205 may be configured for activating both the chemical heater and for dispensing the source of humidification fluid to the chamber; optionally the activation and dispensing may occur simultaneously or in a substantially simultaneous operation.

It may also be desirable to position the trigger in a position that best avoids accidental activation prior to actual use. The trigger may also comprise of an indicator to visually display whether the trigger can be activated or not.

Where the trigger may comprise of a humidification fluid reservoir 207, the fluid reservoir is initially sealed from the chamber 201 prior to use (i.e. when in a storage condition), and where the fluid reservoir 207 can be unsealed (e.g. the seal can be broken or pierced or otherwise opened) for dispensing of the fluid 206 to the chamber 201 when the device is put into use.

In one form, the trigger may be (or comprise of) a plunger 208 received within a humidification fluid reservoir 207 that is sealed from the chamber when in a pre-use configuration, and where fluid stored in the fluid reservoir is then unsealed and fluid dispensed into the chamber when in an in-use configuration. Stroking the plunger within the fluid reservoir breaks a seal 213 between the fluid reservoir and the chamber. The plunger seals against the walls of the reservoir to seal the reservoir from the external environment. Once the seal between the fluid reservoir and the chamber is broken the plunger also seals the chamber from the external environment.

The trigger 205 is able to activate the chemical heater 204 and/or dispense the humidification fluid to the chamber when operated and moved from a pre-use configuration to an in-use configuration.

The trigger can be any suitable mechanism that activates the chemical heater to begin generating heat.

In various forms however, the trigger can be a mechanical actuator that, when actuated, provides for a nucleation site within the chemical heating element to initiate a crystallisation. For example, the trigger may comprise a metallic disk that is optionally located within the chemical heater or a part thereof.

Where sodium acetate is used, the metallic disk, when triggered or actuated, by for example plunger 205, may release a particle that initiates an exothermic crystallisation process.

The chemical heater 204 is disposed in thermal exchange with (or may at least be in contact with a part of) a base or base portion 209 of the chamber. The chamber base or base portion can be heat conductive and may form a, or the, floor 209 of the chamber 201. In the illustrated embodiment the base defines a cavity 210 that contains the chemical heater 204. Preferably the chamber is formed between a heat conductive portion 209 directly or indirectly in thermal exchange with the chamber or forming the floor of the chamber, and a foot or outer thermally insulating part 211. The insulating foot restricts heat conduction to the surrounding environment.

Alternatively, the chemical heater may be disposed at least in thermal exchange or conduction with a heating surface disposed between the chemical heater and a floor or base of the chamber.

Figure 8:
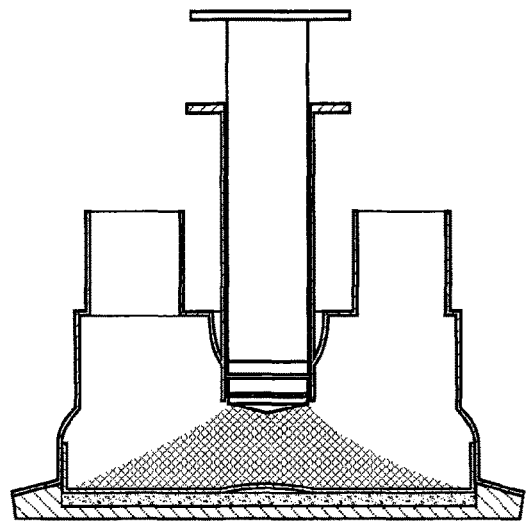
FIG. 8 is a cross sectional representation of the device of FIG. 6 illustrating the dispensing of humidification fluid into the chamber.
Figure 9:
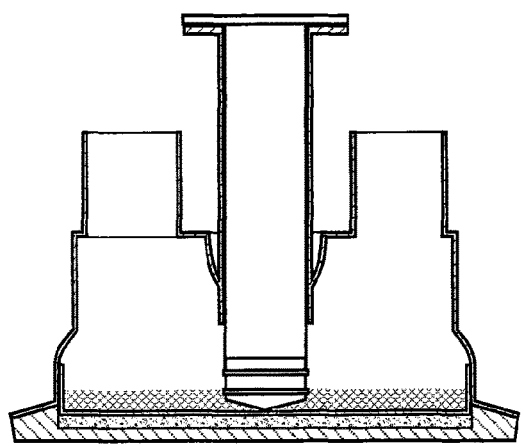
FIG. 9 is a cross sectional representation of the device of FIG. 6 illustrating the triggering of a chemical heater in a base of the device.

In the illustrated embodiment the trigger comprises the plunger 208 that is adapted to stroke within the reservoir towards the chamber to dispense the fluid into the chamber, and a metallic disk 212 that is located within the chemical heater or a part thereof. In the illustrated embodiment the metallic disk is integrally formed with the floor of the chamber. In use the plunger is stroked towards the chamber floor to initially pressurise the fluid in the reservoir to break the seal 213 between the reservoir and the chamber. Once the seal 213 is broken, the fluid dispenses from the reservoir and into the chamber as shown in FIG. 8. The user or health profession continues to stroke the plunger towards the chamber floor until the plunger contacts the metallic disk integrally formed in the chamber floor. Pressing the plunger against the disk deforms the disk so that the disk releases a particle within the chemical heater that initiates an exothermic crystallisation process.

In an alternative form a metallic disk is located within the chemical heater below the chamber floor. A bulge projecting into the chamber is formed in the chamber floor. In a similar operation as described above, the plunger contacts the bulge in the chamber floor to deform into the chemical heater. The metallic disk is located below the bulge and is deformed as the bulge in the floor is deformed to activate the chemical heater.

Figure 10:
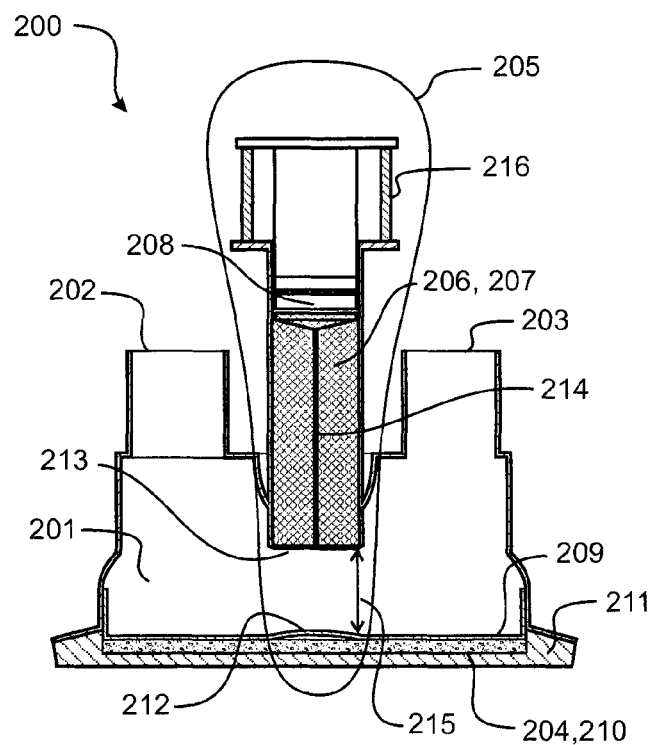
FIG. 10 is a cross sectional representation of another form of the device of FIG. 6.

In a further form as illustrated in FIG. 10, the trigger comprises the plunger, the metallic disk, and a pin or extension member 214 extending from the plunger towards the chamber floor. During use, a user or healthcare practitioner pressed the plunger towards the chamber floor. The tip of the extension member distal from the plunger pierces the seal 213 to allow the fluid to dispense into the chamber. Continuing to press the plunger into the reservoir strokes the extension member towards the chamber floor until the tip of the extension member contacts and depresses the metallic disk or bulge 212 in the floor of the chamber to activate the chemical heater. In this form, the extension member 214 breaks the seal 213 and activates the chemical heater 204. And the stroke of the plunger and extension member only needs to be equal to or slightly greater than the distance 215 between the seal 213 and the floor 209 of the chamber.

Preferably a mechanism is provided to prevent inadvertent dispensing of fluid into the chamber or activation of the chemical heater. For example, a removable spacer 216 could be provided, one end of which bears against a member coupled to the plunger and an opposite end that bears against a member coupled to the reservoir to prevent the plunger being stroked toward the chamber floor. To operate the plunger the user removes the spacer so that it can be stroked towards the chamber floor. For example the spacer could be an open ended cylinder with a longitudinal split.

The chemical heater may comprise or is a chemical agent that, when activated, is exothermic or generates heat. In one example, the chemical heater may be a supersaturated salt solution capable of undergoing an exothermic reaction, such as during a crystallization process, that process being carried out or initiated when activated by a trigger. The chemical heater element may for example be sodium acetate (e.g. a supersaturated solution of sodium acetate that when activated, undergoes an exothermic crystallisation process).

According to this embodiment, the inlet and outlet and the chamber can be defining of a gas transport pathway therebetween.

In a further form, there may be provided a device for humidifying breathing gas. The device comprises a chamber for humidifying gas, the chamber having an inlet connectable with, or fluidly connectable to, a gas supply, and an outlet connectable with, or fluidly connectable to, a user interface or a user gas delivery device. A chemical heater can be disposed for thermal exchange with at least a part of the chamber, and a trigger being configured for activating the chemical heater to generate heat. A source of humidification fluid is provided that is dispensable to the chamber. Accordingly, in use, on activation the humidification fluid is dispensed to the chamber and the chemical heater generates heat for heating of gas passing through the chamber and/or promotes humidification fluid uptake by the gas.

In yet a further form, the above embodiment may be a chemically powered heater for humidifier, where the heater is located within base of chamber, the chamber has gas inlet and gas outlet, and a trigger for activating the chemical heater and for administering humidification fluid to the chamber.

Method of Operation

In a further embodiment, there is provided a method for humidifying breathing gas.

The method comprising: providing a gas transport pathway between an inlet and an outlet, and providing a chemical heater disposed in thermal exchange with at least a part of the gas transport pathway, and a trigger for activating the chemical heater to generate heat, and providing a source of humidification fluid, the humidification fluid being made available for uptake by gas passing through the gas transport pathway upon activation of the chemical heater.

According to the embodiment above, there can be further provided an inner wall of a conduit arrangement defines the gas transport pathway, the conduit arrangement comprising of the inner wall and an outer wall, the outer wall surrounding at least a section of the inner wall, wherein a reservoir is defined between the inner and outer walls, the chemical heater located within the reservoir, and wherein the source of humidifying fluid is contained within the outer wall, and the trigger is configured for activating the chemical heater to generate heat. In this manner, in use, on activation by the trigger, the chemical heater generates heat for heating of gas passing through the gas transport pathway and/or promotes humidification fluid uptake by the gas.

And, according to the embodiment above, in an alternative, the gas transport pathway can be defined between the inlet and the outlet of a chamber, with a chemical heater disposed for thermal exchange with at least a part of the chamber. The source of humidification fluid is dispensable to the chamber on activation of the trigger, and in the same operation, the trigger activates the chemical heater to generate heat. In this manner, in use, on activation by the trigger, the humidification fluid is dispensed to the chamber and the chemical heater generates heat for heating of gas passing through the chamber and/or promotes humidification fluid uptake by the gas.

In respect of the various embodiments above, the inlet is connectable with, or fluidly connectable to, a gas supply. And, the outlet is connectable with, or fluidly connectable to, a user interface or a user gas delivery device. In configuring the device in this way, during an in-use configuration, gas passing through the gas transport pathway can be heated and/or is humidified by uptake of humidification fluid. It will be appreciated the gas supply can be provided from a blower or a ventilator or a resuscitator. In addition, the user interface may be a mask or a nasal cannula or other suitable device for delivering of heated and/or humidified gas from the device to a user or patient. The user gas delivery device can be or comprise at least a part of a medical breathing circuit, such as a further section of conduit or other gas delivery device for supplying of the heated and/or humidified gas to a user or patient.

With respect to the above devices of this invention as described above, one possible chemical heating agent is a supersaturated salt solution that undergoes and exothermic crystallisation process. The crystallisation process may be trigger by depositing a nucleation site within the chemical heating agent. And, one form of a mechanical trigger suitable for activating a chemical heating agent comprising a saturated salt solution is a depressible button. The button trigger may be formed as a metallic disk that deposits a ferrous metal particle or salt crystal into the chemical heating agent to create a nucleation site and initiate crystallisation.

Sodium acetate trihydrate (commonly referred to as sodium acetate or sodium ethanoate ($NaC_2H_3O_2$ or NaOAc) is a crystalline salt that forms a particularly desirable chemical heater agent. Sodium acetate crystals melt at about 58° C., dissolving in their water of crystallisation. Then the solution is heated to about 100° C., and subsequently allowed to cool, in doing so the aqueous solution becomes supersaturated. Crystallisation of sodium acetate occurs at a latent heat of about 264 to 2891 d/kg. This heat is generated rapidly and can be sustained for periods commonly encountered during resuscitation and other similar emergency respiratory applications. These process characteristics make sodium acetate a particularly desirable chemical heating agent for a respiratory humidifier.

There are a number of associated advantages with the devices described above, including for example, but not limited to, that the device does not need to rely upon an electrical source for operation. For example, during a power failure, or during a field operation, the device can be operated independently (the gas source may be provided from a set of manual bellows or other suitable gas supplier). The device is portable, but may still be utilised in a hospital environment, but has the advantage of not requiring any additional parts itself or other sources of power to be operated. It will also be appreciated the gas source or supply is preferentially a supply of breathing gas, although could have other application to other gases or medical gases.

The devices of this invention may be provided with sufficient humidification fluid to enable humidification of gases for a period of time.

The device of this invention may have particular application as a part of a medical breathing circuit, or a medical resuscitation system.

The device may also particular application as a single-use device. For example, once the device is activated, the chemical heater operates until no further heat is generated and/or the humidification fluid is wholly used up from within the device.

As described above with reference to FIG. 1, a typical respiratory humidifier setup usually comprises a humidifier chamber 5 with an electrically powered heater 7 in thermal contact with the chamber 5 and the humidification fluid contained inside. In this manner, when the heater 7 is switched on, the humidification fluid is heated and vapour generated. That vapour is taken up by gas passing through the chamber 5 from an inlet 12 and exiting via an outlet 4. The gas is supplied to the inlet 12 from a source or supply, such as a blower or ventilator system, generally indicated by 11. The gas travels from the source to the chamber via a first conduit, through the humidification chamber 5, then onwards via one or more further conduits 3, for delivery or administration to a user interface 2, such as a mask.

According to the first embodiment as described above, the humidification chamber 5 and heater base 7 as required by a typical setup shown by FIG. 1 can be eliminated. In their place is instead provided the device 100 as for example shown in FIG. 2. The device 100 avoids the need for a separate humidification chamber provided in combination with an electrically operable heater base.

According to the second embodiment as described above, in comparison with a typical setup as shown by FIG. 1, there is no need to provide an electrically powered heater base 7 for warming of humidification fluid in a humidification chamber 5. The device 200 avoids the need for an electrically operable heater base to be provided for warming of humidification fluid or gas passing through the chamber.

In respect of both devices 100 and 200, such devices can be supplied with breathing gases, or gases to be heated and/or humidified, by any means available. For example, manual or electric or other powered bellows, manual or electric or other powered ventilator systems or suitable systems for provided gas in a form for resuscitation procedures. How gases are supplied for warming and/or humidification by these devices 100, 200 may be determined by where the user of the device is, for example if in a hospital, the gas can be supplied from a known source or if in a remote rural location (i.e. not a hospital) the gas could, for example, be supplied by a set of manual bellows.

The invention claimed is:

1. A device for humidifying breathing gas comprising:
   a coaxial tubing arrangement, the coaxial tubing arrangement comprising an inner tube and an outer tube, the inner tube defining a gas transport pathway, the gas transport pathway including an inlet and an outlet, the outer tube coaxial with and surrounding at least a section of the inner tube,
   wherein a reservoir is defined between the inner tube and the outer tube,
   wherein a chemical heater is located within the reservoir,
   wherein a source of humidifying fluid is contained by the outer tube, and
   wherein a trigger is configured for activating the chemical heater to generate heat.

2. The device as claimed in claim 1, wherein the inlet is configured to be connected to a gas supply, and the outlet is configured to be connected to a user interface or a user gas delivery device.

3. The device as claimed in claim 1, wherein the chemical heater is disposed for thermal exchange with at least a part of one or more selected from the group consisting of the inner tube, the section of inner tube, a gas passing through the gas transport pathway, and the humidifying fluid.

4. The device as claimed in claim 1, wherein the source of humidifying fluid is provided from within or by one or more selected from the group consisting of the inner tube, the section of inner tube, and the reservoir, wherein the humidifying fluid is for humidifying a gas passing through the gas transport pathway.

5. The device as claimed in claim 1, wherein the source of humidifying fluid is located within the reservoir.

6. The device as claimed in claim 1, wherein the source of humidifying fluid is provided from within the reservoir.

7. The device as claimed in claim 1, wherein, on activation, the chemical heater generates heat for heating of a gas passing through the gas transport pathway or promotes humidifying fluid uptake by the gas.

8. The device as claimed in claim 1, wherein, when activated, the chemical heater generates heat and provides a source of the humidifying fluid.

9. The device as claimed in claim 1, wherein the inner tube is breathable.

10. The device as claimed in claim 1, wherein the inner tube is configured to allow passage of the humidifying fluid to a gas passing through the gas transport pathway.

11. The device as claimed in claim 1, wherein the inner tube is configured to allow passage of a vapor of the humidifying fluid to a gas passing through the gas transport pathway.

12. The device as claimed in claim 1, wherein the inner tube is configured to store humidifying fluid, such that, in-use, a gas passing through the gas transport pathway takes up at least a portion of the stored humidifying fluid.

13. The device as claimed in claim 1, wherein the inner tube is pre-charged with humidifying fluid prior to use.

14. The device as claimed in claim 1, wherein the reservoir is configured to be capable of storing humidifying fluid, such that, in-use, the humidifying fluid, or vapour thereof, and a gas passing through the gas transport pathway are fluidly contactable.

15. The device as claimed in claim 1, wherein the chemical heater is a chemical agent that, when activated, is exothermic.

16. The device as claimed in claim 1, wherein the chemical heater is a supersaturated salt solution capable of an exothermic crystallization when activated.

17. The device as claimed in claim 1, wherein the chemical heater comprises sodium acetate.

18. The device as claimed in claim 1, wherein the trigger is a mechanical actuator that, when actuated, provides for a nucleation site within the chemical heater to initiate a crystallization.

19. The device as claimed in claim 1, wherein the device is single use.

20. A device for humidifying breathing gas comprising:
   an inner tube defining a gas transport pathway, the gas transport pathway including an inlet configured to be connected to a gas supply, and an outlet configured to be connected to a user interface or a user gas delivery device,
   an outer tube surrounding the inner tube or a section of the inner tube, the outer tube is impermeable to humidification fluid or vapour,
   a reservoir defined between the inner tube and the outer tube,
   a chemical heater located within the reservoir, the chemical heater configured for thermal exchange with one or more selected from the group consisting of an inner wall of the inner tube, a section of the inner wall of the inner tube, a gas passing through the gas transport pathway, and a humidifying fluid, and
   wherein a source of humidifying fluid is provided from within or by one or more selected from the group consisting of the inner wall of the inner tube, the section of the inner wall of the inner tube, and the reservoir, wherein the humidifying fluid is configured for humidifying the gas passing through the gas transport pathway, a trigger configured for activating the chemical heater to generate heat, wherein, on activation, the chemical heater generates heat for heating of the gas passing through the gas transport pathway or promotes humidifying fluid uptake by the gas.

21. A method for humidifying breathing gas comprising:

providing a gas transport pathway between an inlet and an outlet, providing a chemical heater disposed in thermal exchange with at least a part of the gas transport pathway, and a trigger configured for activating the chemical heater to generate heat, and providing a source of humidifying fluid, the humidifying fluid being made available for uptake by a gas passing through the gas transport pathway upon activation of the chemical heater, wherein an inner tube of a coaxial tubing arrangement defines the gas transport pathway, the coaxial tubing arrangement comprising the inner tube and an outer tube, the outer tube coaxial with and surrounding at least a section of the inner tube, and wherein a reservoir is defined between the inner tube and the outer tube, the chemical heater located within the reservoir, and wherein the source of humidifying fluid is contained by the outer tube.

22. The method as claimed in claim 21, further comprising pre-charging the coaxial tubing arrangement with humidifying fluid during manufacturing of the coaxial tubing arrangement.

* * * * *